United States Patent [19]

De Witte

[11] Plant 4,083

[45] July 26, 1977

[54] ROSE PLANT—JOFITALI VARIETY

[76] Inventor: Willem De Witte, Aarbergerweg 15, Rijsenhout (Post Aalsmeer) Commune de Haarlemmeneer, Netherlands

[21] Appl. No.: 689,503

[22] Filed: May 24, 1976

[30] Foreign Application Priority Data

May 28, 1975 Netherlands ..... 752882
Oct. 31, 1975 Morocco ..... 17283

[51] Int. Cl.[2] ..... A01H 5/00
[52] U.S. Cl. ..... Plt./19

[58] Field of Search ..... Plt./19

*Primary Examiner*—Robert E. Bagwill
*Attorney, Agent, or Firm*—Burns, Doane, Swecker & Mathis

[57] ABSTRACT

A rose plant of the Grandiflora Class, obtained as a bud mutation of the variety Sweet Promise (known in the United States as Sonia) (U.S. Plant Pat. No. 3,095). The flower of this new variety is Rose Bengal on the inside and Spiraea Red on the outside.

13 Drawing Figures

SUMMARY OF THE INVENTION

The object of the present invention is a variety of rose-plant of the Grandiflora Class, whose vegetative type corresponds to that of the variety Sweet Promise, (known in the United States as Sonia) (U.S. Plant Pat. No. 3,095) but whose flowers, although of the same form, are distinguishable because of a very luminous Rose Bengal color, instead of Porcelain Pink touched up with Begonia Pink in depth.

The variety of rose-plant, object of the present invention, is the result of a selective study carried out on numerous plants formed by grafting the new matter (new eye-bud) arising from a bud mutation of the said variety Sweet Promise.

In view of the interest that would be created, in the horticultural industry, by the disclosure of the different technical effect presented by the new variety as compared with the original variety, it was advisable to propagate the said new variety on a large scale in order to check its behavior, from the physical as well as the biological point of view.

The results were conclusive and underlined the importance of disclosing such a variety, with a view to its industrial exploitation by the professional nurserymen and the producers of cut flowers.

The characters and properties of this new variety, obtained as indicated above are strictly transmissible by agamic means, also called "asexual", i.e., by any means of vegetative propagation, in particular by grafting an "eye" which will be called in the trade by the name of Jofitali 0944 F. NL. and which will be found on industrial plants as well as on cut stems delivered subsequently in the trade.

BRIEF DESCRIPTION OF THE DRAWINGS

The accompanying drawings show as nearly true as it is reasonably possible to make the same in a color illustration of this character, typical specimens of the flowers and foliage, illustrated in.

DETAILED DESCRIPTION OF DISCLOSURE

Figures 1, 2, 3, 4, 5, 6, 7, 8, 9, 10, 11, 12:
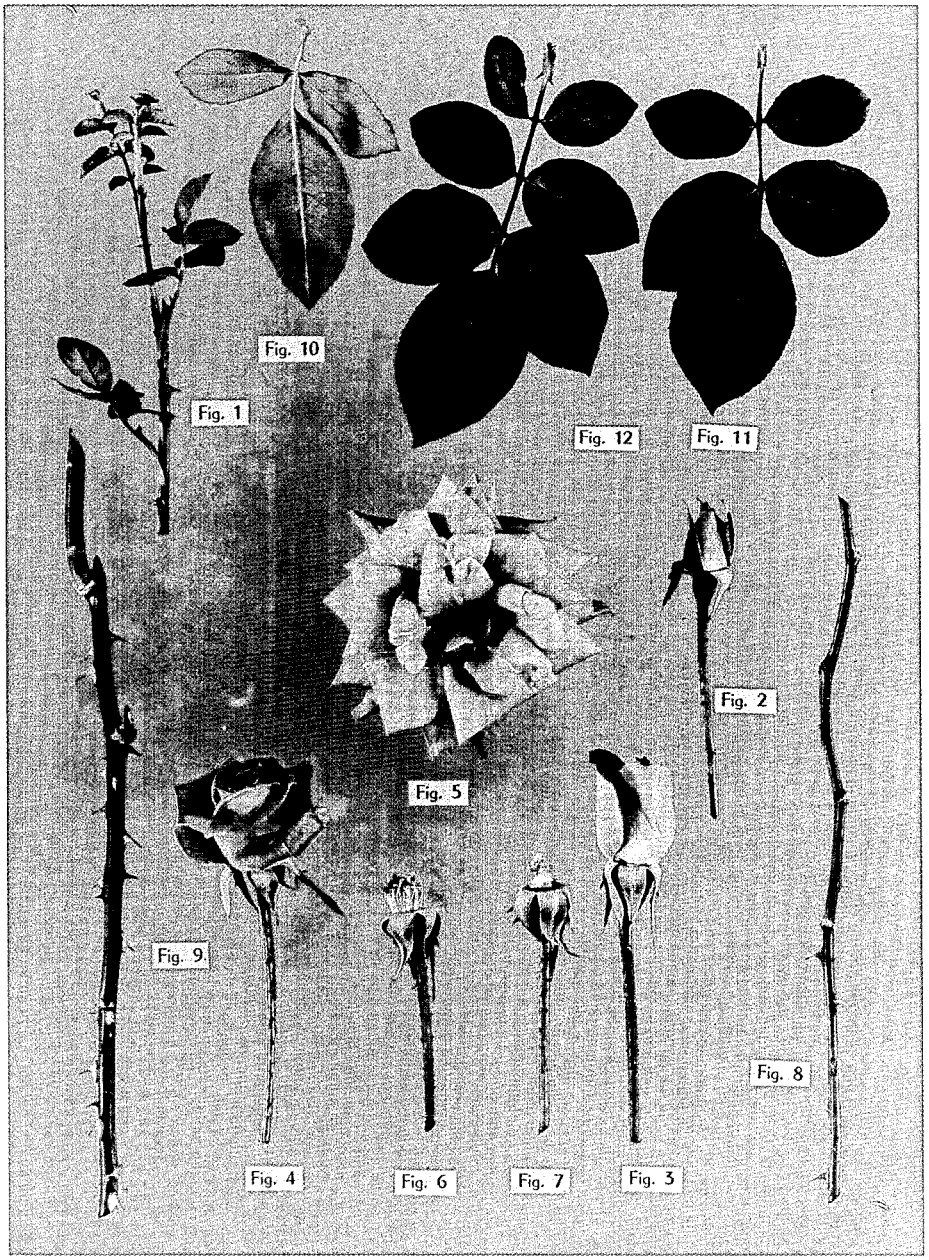
FIG. 1 — a specimen of a young shoot.
FIG. 2 — a specimen of a bud when sepals open.
FIG. 3 — a specimen of a bud when the first petal opens.
FIG. 4 — a specimen of a flower, half-open.
FIG. 5 — a specimen of a flower, fully open, upper surface.
FIG. 6 — a specimen of a receptacle showing at the dehiscence of the anthers the disposition of the stamens.
FIG. 7 — a specimen of a receptacle showing the disposition of the pistils (stamens removed)
FIG. 8 — a portion of a flower bearing stem.
FIG. 9 — a portion of a main branch.
FIG. 10 — a specimen of a 3 foliole leaf, under surface.
FIG. 11 — a specimen of a 5 foliole leaf, upper surface.
FIG. 12 — a specimen of a 7 foliole leaf, upper surface.
Figure 13:
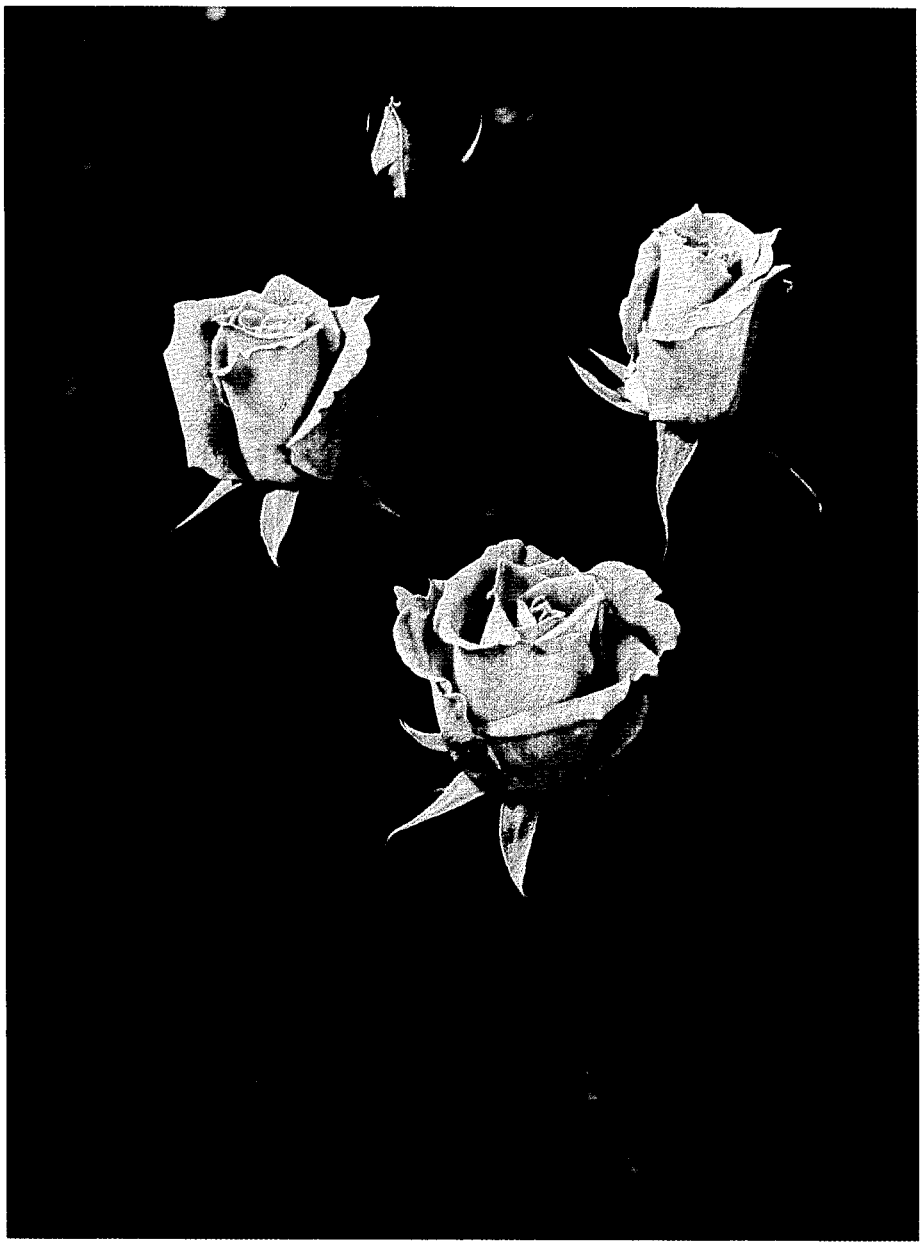
FIG. 13 — a specimen of a bud, flowers, and leaves.

Thus will be obtained once again the rose variety — object of the patent — whose botanical and descriptive characteristics as observed on plants grown under glass in Holland, are listed below:

(The Chart used for the identification of the colors is that of the Royal Horticultural Society (R.H.S. Color Chart). The terminology preceding the numbered references, proper to this Chart, has been added to designate, in common terms, the corresponding colors.)

Class: Grandiflora.

Plant:

*Height.*—On the basis of the cutting back of plants under glass to 0 m 85, the length of the flowering stems to be cut is 60 cm. on an average.

*Habit.*—Erect.

Branches:

*Color.*—Young stems: Lettuce Green 146/D yellow green group on the shaded parts, reddish brown (common term) on the sunlit parts. Mature wood: Medium green 137/C green group.

*Prickles.*—Shape: upper edge straight; lower edge concave; size: medium; quantity: average, presence of acicules; color on young stems: reddish (common term); on mature wood: greenish pink, straw then Havana brown (common terms).

Leaves:

*Stipules.*—Adnate, pectinate, fairly narrow and relatively short.

*Petiole.*—Obverse: young leaf: the vein is tinted with reddish brown; adult leaf: light green, edges slightly glandular. Reverse: light green, with a few small hooked prickles.

*Folioles.*—Number: 3, 5 or 7, rarely 9; shape: elliptical, with pointed tip; length of a 7 foliole leaf: 145 mm; width of a 7 foliole leaf: 100 mm; teeth: single, even; texture: leathery; general effect: dull foliage, of medium density, fairly ample; color, young foliage, upper surface: medium green 137/C green group; the median vein and the teeth of the edges of the petioles are tinted with red; under surface: greyish green 191/B greyed green group, more or less suffused with red; adult foliage, upper surface: dark green 130/A green group; under surface: greyish green 191/A greyed green group.

Inflorescence:

*Number of flowers.*—Generally one flower per stem.

*Peduncle.*—light green, straight, rigid; it shows numerous small pediculate glands and a few tiny prickles without consistence. Length: 8 cm. on an average.

*Sepals.*—Normal, pectinate, relatively wide, hairy and whitish inside, light green more or less stained with red outside, with small pedicellate glands. Length: 28 mm. Width: 12 mm.

*Bud.*—Shape: elongated; length: 25 mm outside the calyx, when sepals start to open; width: 12 mm; size: medium; color: when opening — inside: Cardinal Red 53/C (red group); Satin-like Cardinal Red 53/B towards the center; outside: Rose Red 58/B (red purple group).

*Flower.*—Form: initially high-centered, then when open projecting and overlapping petals. The unguis is yellowish white (common term) on both sides. Double flower — diameter: 9 cm. on an average; color, at the opening — inside: Rose Bengal 57/B (red purple group), very luminous, more or less shaded with Cardinal Red 53/B (red group) towards center; outside: Rose Red 58/B (red purple group); while opening — inside: Rose Bengal 57/B (red purple group) very luminous, more or less stained with Cardinal Red 53/B (Red group) towards center; outside: Spiraea Red 63/C (Red purple group) in depth, more or less shaded with Rose red 58/B (Red purple group); when fully open — inside: Rose Bengal 57/C (Red Purple group) luminous more or less shaded with Cardinal Red 53/C (Red group) towards the center; outside: Spiraea Red 63/C (Red purple group) in depth, more or less shaded with Rose red 58/B (Red purple group); fragrance: very light; lasting quality: long — on the plant as well as when cut; corolla — petals — texture: very consistent; shape: broadly rounded; rounded tip that can be slightly wavy — the central petals are not always entire and possess very pronounced indentations as well as whitish median veins. The unguis is yellowish white (common term) on both sides; number: 25–30. The petals fall off cleanly. Stamens — number: 130 on the average; anthers: normal, yellow; filaments: of uneven length, they are either yellowish or tinted with pink; pistils — number: 75 on the average; stigmas: normal, whitish on the level of the anthers; styles: yellowish at base, fuchsine on the level of the stigmas; more or less twisted. Receptacle: smooth, light green; it is narrow and in the shape of a pitcher when cut lengthwise.

Development:

*Vegetation.*—Very vigorous.

*Capacity for re-blooming.*—Excellent.

*Resistance to diseases.*—Great.

I claim:

1. A new and distinct variety of Grandiflora rose-plant of vegetative reproduction, characterized by the fact that from the physical point of view, the plant is erect; the flower is double, very luminous Rose Bengal on the inside and Spiraea Red on the outside; the flower initially has a high-centered form;

from the biological point of view, this rose-plant is of vigorous vegetation, has an excellent capacity for reblooming, great resistance to diseases, and its flowers last a long time whether on the plant or when cut;

substantially as shown and described.

* * * * *